United States Patent [19]
Uzan et al.

[11] Patent Number: 5,849,247
[45] Date of Patent: Dec. 15, 1998

[54] AUTOMATIC APPARATUS FOR IMMUNOLOGICAL ASSAY

[75] Inventors: Michel Uzan, Pavillons-Sous-Bois; Thierry Gicquel, Courdimanchie, both of France

[73] Assignee: Merck S.A., Cedex, France

[21] Appl. No.: 666,522

[22] PCT Filed: Oct. 25, 1995

[86] PCT No.: PCT/FR95/01414

§ 371 Date: Jul. 29, 1996

§ 102(e) Date: Jul. 29, 1996

[87] PCT Pub. No.: WO96/14582

PCT Pub. Date: May 17, 1996

[30] Foreign Application Priority Data

Nov. 7, 1994 [FR] France .................................. 94 13297
Jun. 23, 1995 [FR] France .................................. 95 07564

[51] Int. Cl.⁶ .................................................. G01N 35/02
[52] U.S. Cl. .............................. 422/65; 422/63; 422/64; 422/67; 422/82.05; 436/43; 436/47; 436/48; 436/49; 436/165
[58] Field of Search ................................. 422/63, 64, 65, 422/102, 103, 104, 67; 436/43, 47, 48, 49, 164, 172, 174, 179, 180, 165

[56] References Cited

U.S. PATENT DOCUMENTS

| 3,897,216 | 7/1975 | Jones .................................... 422/65 |
| 4,236,825 | 12/1980 | Gilford et al. ..................... 356/414 |
| 4,265,855 | 5/1981 | Mandle et al. ....................... 422/65 |
| 4,578,244 | 3/1986 | Cosgrove, Jr. et al. ............ 422/65 |
| 4,668,617 | 5/1987 | Futura et al. ......................... 435/4 |
| 4,710,352 | 12/1987 | Slater et al. ........................ 422/63 |
| 4,731,225 | 3/1988 | Wakatake ............................ 422/65 |
| 4,861,554 | 8/1989 | Sakuma ............................... 422/65 |
| 4,882,127 | 11/1989 | Rosenthal et al. ................... 422/50 |
| 5,096,670 | 3/1992 | Harris et al. ........................ 422/65 |
| 5,232,665 | 8/1993 | Burkovich et al. .................. 422/65 |
| 5,397,539 | 3/1995 | Hayashi et al. ...................... 422/65 |

*Primary Examiner*—Long V. Le
*Attorney, Agent, or Firm*—Bell Seltzer Intellectual Property Law Group of Alston & Bird LLP

[57] ABSTRACT

Automatic immunological assay apparatus comprising reaction wells in which there are deposited quantities of samples to be analyzed and of reagents, the reaction wells being grouped in modules (40) that are moved in translation, sliding between rails that define a U-shaped track (24), running from automatic reaction well feed device (26) to device (28) for ejecting the wells after use.

16 Claims, 7 Drawing Sheets

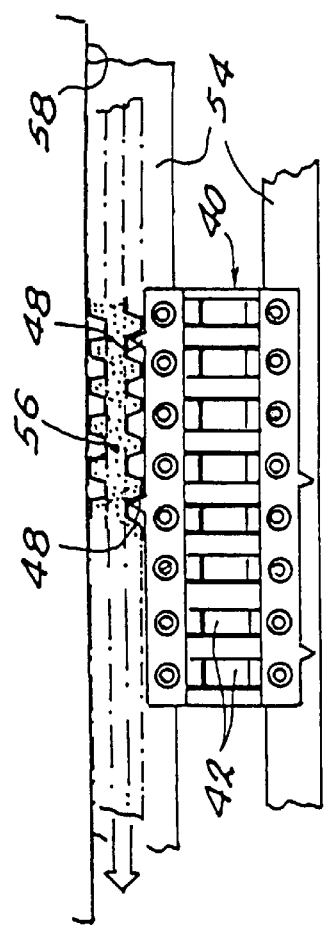
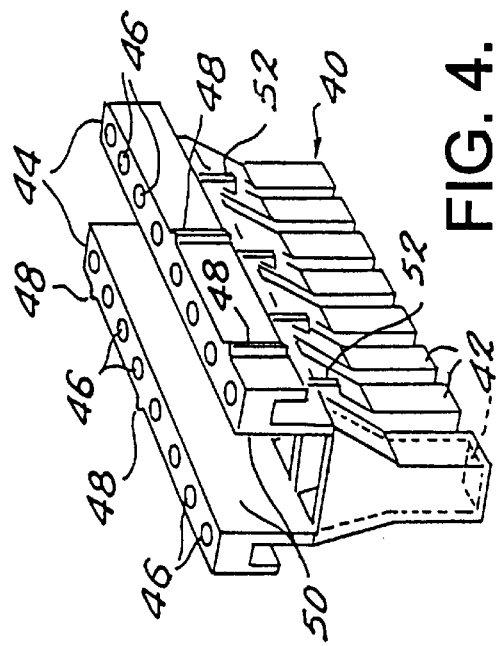
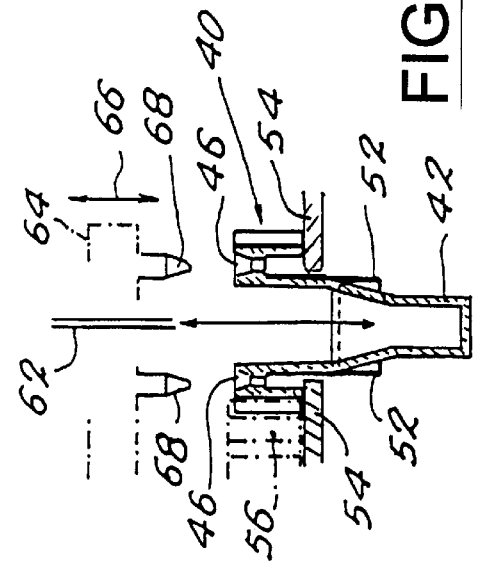
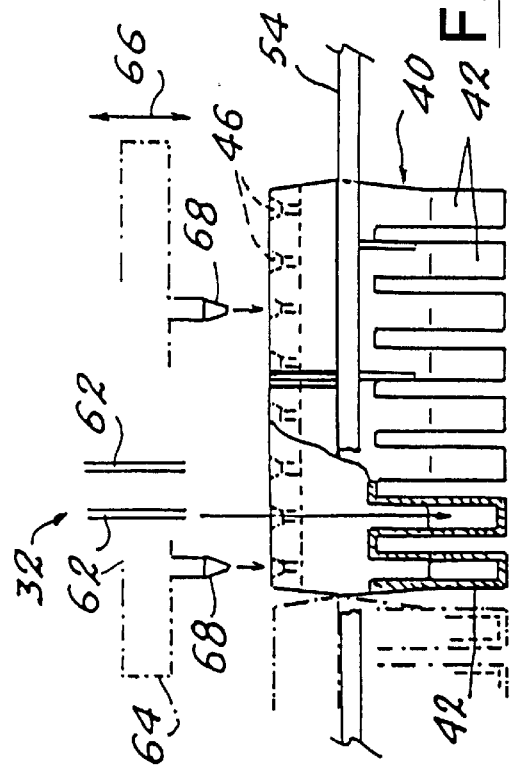

AUTOMATIC APPARATUS FOR IMMUNOLOGICAL ASSAY

The present invention relates to apparatus for immunological assay of various substances in biological samples, and suitable for fully automating the assay methods in use, which methods are of the following types: ELISA, RIA, FIA, LIA, FPIA, CLIA, etc.

Apparatus of this type has already been described in international application WO 91/07662, to which reference may be made for a more detailed description of the assays performed, that known apparatus essentially comprising three turntables respectively carrying about 100 reaction wells, reagents, and samples to be analyzed, means enabling samples and reagents to be taken and placed in the reaction wells, means for reading the results of the assay optically, and a controlling computer system enabling preprogrammed analysis cycles to be performed, which cycles require two complete revolutions of the turntable carrying the reaction wells when performing single-reagent type assays, and three complete revolutions of said turntable when performing dual-reagent type assays, thereby enabling throughput at a rate of about 100 assays per hour, which result is already quite remarkable compared with the competition.

The present invention seeks in particular to increase the performance of that known apparatus very considerably.

To this end it provides an automatic immunological assay apparatus, comprising reaction wells, means for supporting samples to be analyzed, means for supporting reagents, means for taking determined quantities of samples and of reagents and depositing them in the reaction wells, means for reading assay results, and means for displacing the wells stepwise past the means for taking samples and reagents and the means for reading the results, the apparatus being characterized in that the reaction wells are grouped in modules each formed as a single piece and comprising a certain number of longitudinally juxtaposed reaction wells, the modules being supported and guided by fixed elements defining an open loop track along which there extends a chain or belt that engages the side faces of the modules to move them from one end of said track to the other end, automatic module feed means and module ejection means being provided respectively at the upstream end and at the downstream end of said track.

In this way, the modules in which the reaction wells are formed are entrained in the apparatus of the invention from one end to the other of a displacement track whose length is determined as a function of the maximum duration of the assays to be performed, thereby avoiding any need to pass the wells two or three times in succession through the same places.

When the reaction wells are advanced by one step every 10 seconds, the known apparatus described in the above-mentioned PCT international application operates at about 120 assays per hour, whereas the apparatus of the invention operates at 360 assays per hour, so its throughput is three times greater than that of the known apparatus.

Advantageously, the track on which the modules move is U-shaped.

The wells are thus moved in one direction along one of the branches of the U-shape, and then in the other direction along the other branch of the U-shape, thereby making it possible to halve the total length of the apparatus and thus reduce its overall size.

In a preferred embodiment of the invention, the fixed elements for supporting and guiding the modules are rails between which the wells extend vertically, and the means for displacing the modules comprise a cog belt or chain engaging with the side faces of the modules, the modules being driven in translation and being displaced by sliding over the above-mentioned rails or fixed elements.

An important advantage of the invention is that the modules formed with the reaction wells are easily mass-produced at very low price, which makes it possible to discard them after a single use.

Further, these modules are easier to store, to handle, to move, and to guide than are individual reaction wells, and they are also stackable in one another, thereby facilitating packaging and stacking in the feed means of the apparatus.

The invention will be better understood and other characteristics, details, and advantages thereof will appear more clearly on reading the following description given by way of example and made with reference to the accompanying drawings, in which:

FIG. 4 is diagrammatic perspective view of a reaction module;

FIG. 5 is a fragmentary diagrammatic view from above of the means for guiding and driving reaction modules through the apparatus of the invention;

FIGS. 6 and 7 are an elevation view and a cross-section respectively of the means for positioning reaction modules in the washing or rinsing stations;

Figure 1:
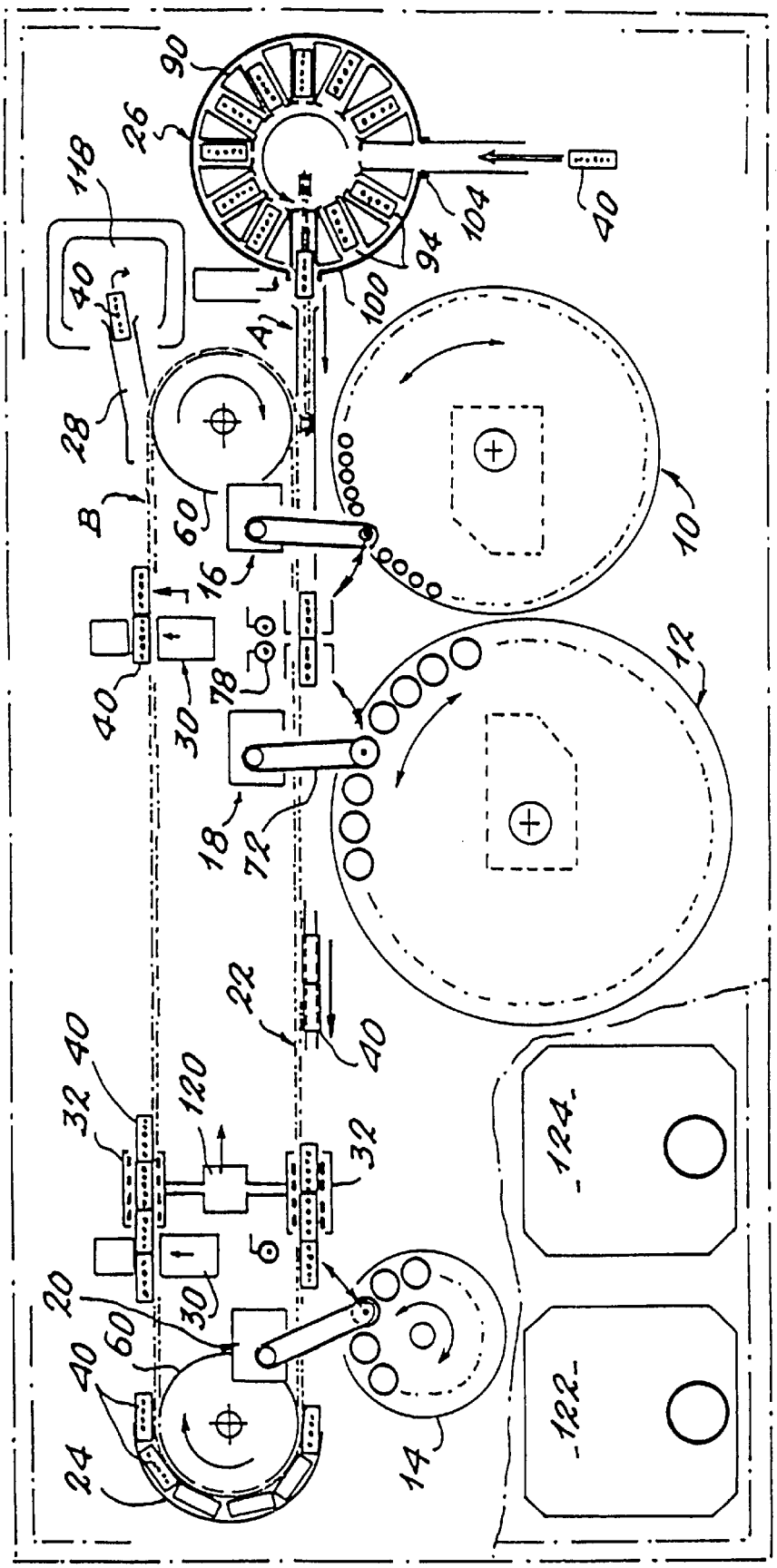
FIG. 1 is a diagrammatic plan view of the apparatus of the invention.
Figure 2:
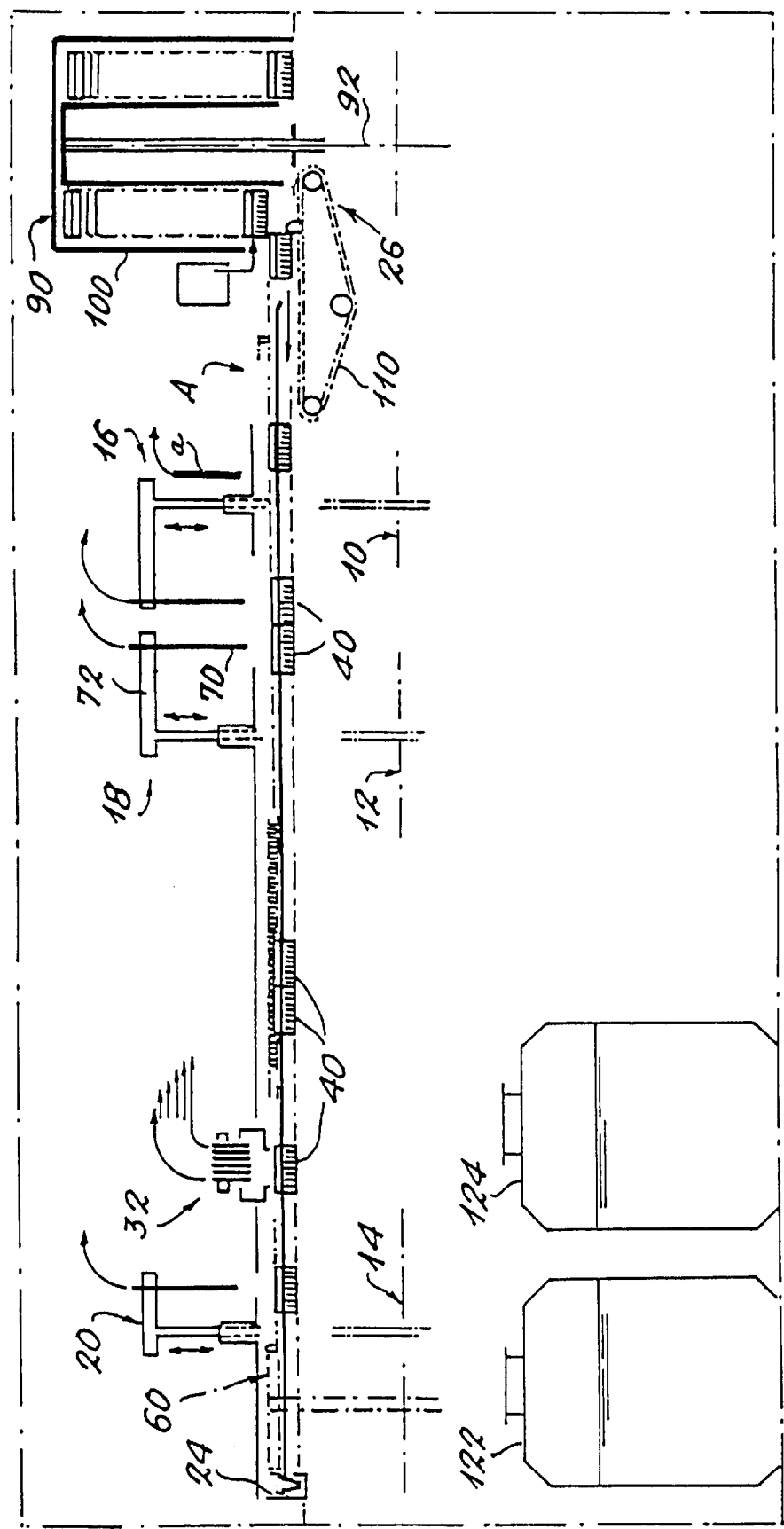
FIGS. 2 and 3 are elevation views of the front face and the back face respectively of the apparatus of the invention.
Figure 3:
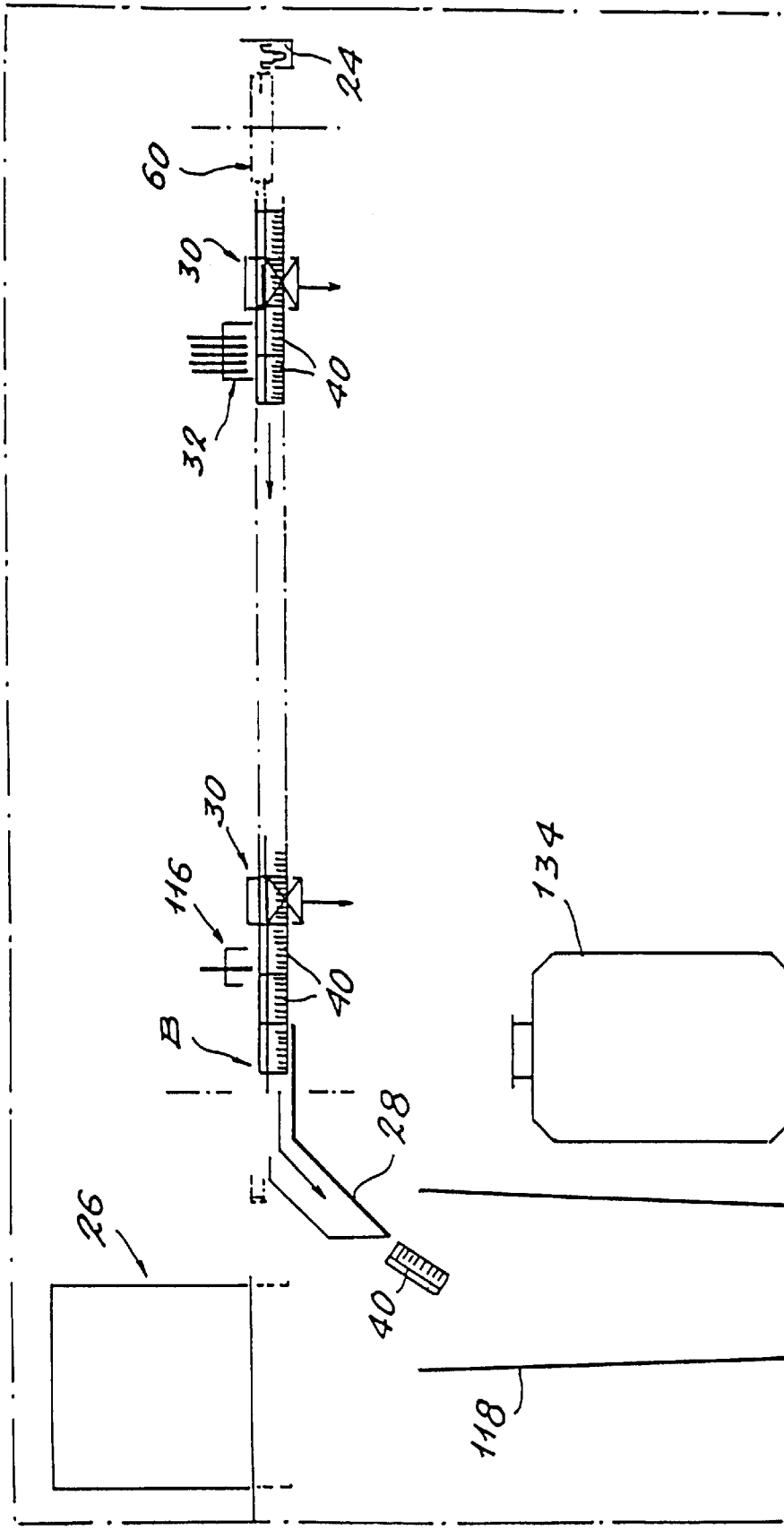

The apparatus of the invention, whose general structure is shown in highly diagrammatic manner in FIGS. 1 to 3, essentially comprises a turntable 10 supporting samples to be analyzed, two turntables 12 and 14 supporting assay reagents, means 16, 18, and 20 for taking a determined quantity of a respective sample or of reagent and for depositing the taken quantity in a reaction well, belt or chain means 22 for driving the reaction wells along a U-shaped track 24, means 26 for feeding the upstream end A of the track 24 with reaction wells, and means 28 for ejecting reaction wells from the downstream end B of the track 24.

In essence, the turntables 10, 12, and 14 for supporting samples and for supporting reagents, and the means 16, 18, and 20 for taking and depositing determined quantities of sample or of reagent are of the same type as those described in above-mentioned international application WO 91/07662, the contents of which is incorporated herein by reference.

The apparatus of the invention also comprises two systems 30 for optically reading assay results, which systems are of the type described in the above-mentioned international application and they are both fed from a common light source.

The reagents used are of the magnetic bead type and the apparatus of the invention includes means 32 for washing or rinsing these magnetic beads, which means are of the same type as those described in the above-mentioned international application and comprise groups of vertically displaceable needles for sucking and injecting liquid, together with permanent magnets disposed on either side of the path of the reaction wells so as to attract the magnetic beads of the reagents by magnetic attraction and hold them temporarily against the walls of the reaction wells.

As described in the above-mentioned international application, a needle for depositing a substrate in the reaction wells is mounted on the washing heads 32 immediately downstream from the needles for injecting and sucking out the washing liquid.

The assays performed by the apparatus of the invention are substantially the same as those performed by the apparatus described in the above-mentioned international application, which explains why many of the means found in that known apparatus are also to be found in the apparatus of the invention. The description now concentrates on the differences between the apparatus of the invention and the apparatus of the above-mentioned international application, which differences relate essentially to the reaction wells, the means for supporting, guiding, and driving the wells, the means for accurately positioning the wells in some of the workstations, and the means for feeding the apparatus with reaction wells.

The apparatus of the invention does not operate with individual reaction wells, but with modules each comprising a certain number of reaction wells, e.g. a number in the range five to ten, which number is equal to eight in the example of FIG. 4.

The reaction modules 40 are formed as single pieces by molding transparent plastics material, and each comprises eight reaction wells 42 that are aligned in a single row in the longitudinal direction of the module 40, together with two top longitudinal rims 44 that are L-shaped and extend along the open ends of the wells 42, securely connecting the wells together.

The top faces of the rims 44 include tapering orifices 46, there being two such orifices associated with each well 42, the orifices serving to position the modules 40 accurately in some of the workstations of the apparatus of the invention. Each of the outside side faces of the rims 44 are formed with two vertical ribs 48 designed to co-operate with the drive means.

The reaction wells 42 are lengths of rectangular section tube, closed at their bottom ends, and flared at their top ends. This makes it possible to stack the reaction modules 40 vertically with them interfitting partially within one another so that the bottom portions of the wells 42 in an upper module 40 penetrate into the flared top portions of the wells 42 of a lower module 40. This interfitting is facilitated by the fact that the inside faces 50 of the longitudinal rims 44 diverge slightly from each other in an upwards direction starting from the open top ends of the wells 42. In addition, vertical ribs 52 are formed on the flanks of the flared top ends of the wells 42 and extend downwards a little way with the right bottom ends of the ribs 52 being designed to come into abutment against the top faces of the rims 44 of a lower module 40 when the modules are stacked vertically, thereby limiting penetration of the upper module into the lower module.

The ribs 52 also serve to limit the areas of contact between the flanks of the modules 40 and the means for guiding them in the apparatus of the invention, as is described below with reference to FIGS. 5 to 7.

The means for supporting, guiding, and driving the reaction modules 40 through the apparatus of the invention are essentially constituted by two parallel rails 54 which define a U-shaped track 24 along which the reaction modules 40 are moved, and by a cog belt 56 which is guided over the top face of the inside rail 54 and against a vertical rim 58 thereof.

The reaction modules 40 rest on the rails 54 via their longitudinal rims 44 so that the reaction wells 42 extend vertically between the rails, with the spacing between the rails being slightly greater than the distance between the edges of the ribs 52 and slightly smaller than the width of the top portion of the reaction module 40.

The cogs of the belt 56 engage the ribs 48 on the corresponding longitudinal rim 44 of the reaction module 40, these ribs 48 being formed near the back and in the middle of the rim 44 of the reaction module 40, whose other rim 44 has corresponding ribs formed near the front and in the middle of the module 40, thereby enabling the module to be engaged either way round on the displacement track 24 while facilitating meshing with the belt 56.

The belt 56 has cogs on both faces, thereby enabling it to mesh with two toothed wheels 60 disposed at opposite ends of the apparatus (FIG. 1), one of the toothed wheels 60 being a driving wheel to cause the belt 56 to move together with the reaction modules 40 in the direction indicated by arrows in FIGS. 1, 2, 3, and 5.

The reaction modules 40 are thus supported by the rails 54, and they move by sliding thereon without significant force being required because of the low weight of the modules 40, because of their small area in contact with the rails 40, and because of the low friction between the materials from which the modules 40 and the rails 54 are made. The spacing between the rails 54 is constant along the entire length of each of the rectangular branches of the U-shaped track 24, and it is slightly wider where the rails from the middle semicircular portion of the track, thereby allowing the reaction modules 40 to turn around the axis of the corresponding toothed wheel 60 while remaining supported and guided by the rails 54.

The reaction modules 40 are brought to and put on the displacement track 24 one after another, and they follow one another along the track forming a continuous or discontinuous row which is moved stepwise by the cog belt 56 over distances equal to the distance between the centers of two successive reaction wells in a module 40, and with the time interval between two advance steps being typically equal to 10 seconds.

Since there is necessarily a certain amount of longitudinal and transverse clearance between the reaction modules 40 and the displacement track defined by the rails 54, means are provided for positioning the reaction modules 40 accurately in those stations of the apparatus of the invention where substances are to be deposited in the reaction wells 40 or where they are to be removed therefrom.

At the heads 32 for washing or rinsing the magnetic beads, which heads comprise a certain number of vertical needles 62 (FIGS. 6 and 7) connected to suction or injection means, the accurate positioning means are constituted by horizontal plates 64 carried by the supports for the needles 62 and vertically displaceable therewith as shown by double-headed arrows 66, the needles 62 passing through the plates 64 with clearance, and the bottom faces of the plates having two rows of vertical fingers 68 with tapering bottom ends that are designed to be engaged in the orifices 46 of the longitudinal rims 44 of the reaction modules, the fingers 68 ensuring very accurate longitudinal and transverse positioning of the reaction modules relative to the needles 62 and enabling the needles to be lowered into the reaction wells 42 down to near the bottoms of the wells without any risk of coming into abutment against a solid wall.

Means for accurately positioning the reaction modules 40 are also provided in association with the means 16, 18, and 20 for taking samples and reagents. As can be seen more clearly in FIGS. 8 and 9, which are diagrams showing the means 18 for taking reagents from the turntable 12 and for depositing the taken reagents in the reaction wells 42, a needle 70 for taking and depositing reagents is carried by a horizontal arm 72 mounted to swing about a vertical axis 74 and displaceable vertically in translation along said axis, thereby enabling the needle 70 to be successively brought vertically over one of the flasks 76 of reagent carried by the turntable 12, lowered into the flask to take a predetermined quantity of reagent, extracted from the flask, swung to a position vertically over the open top end of a reaction well 42, lowered into the inside of the reaction well so as to deposit the taken quantity of reagent, extracted from the well 42, swung to a position vertically over a decontamination pot 78, lowered into the pot to be cleaned by a flow of decontaminating liquid, extracted from the pot 78, and swung back to a position over a flask 76 of reagent.

At these means 18 for taking and depositing reagent, the reaction modules 40 are accurately positioned by a moving arm 80 mounted to pivot about a transverse horizontal axis 81 on the stationary support of the arm 72, and including a fork-shaped end 82 which extends over the path of the reaction modules 40, the bottom face of said end 82 carrying vertical fingers 84 having tapering ends designed to be engaged in the tapering orifices 46 in the top edges 44 of the module 40 on either side of the reaction well 42 into which the needle 70 is to be engaged.

The pivoting arm 80 is returned to its inactive position above the reaction modules 40 by a spring or by gravity, and it is pivoted to its active position by lowering the arm 72, with drive passing via a wheel 86 carried by the arm 72 that bears against an inclined ramp 88 pivotally mounted on the arm 80 and connected thereto by a spring. In a variant, the wheel 86 and the ramp 88 may be replaced by an electromagnet which, when excited, causes the arm 80 to pivot towards its active position, and, when deexcited, returns the arm to its inactive position, or leaves it free to return.

Figure 8:
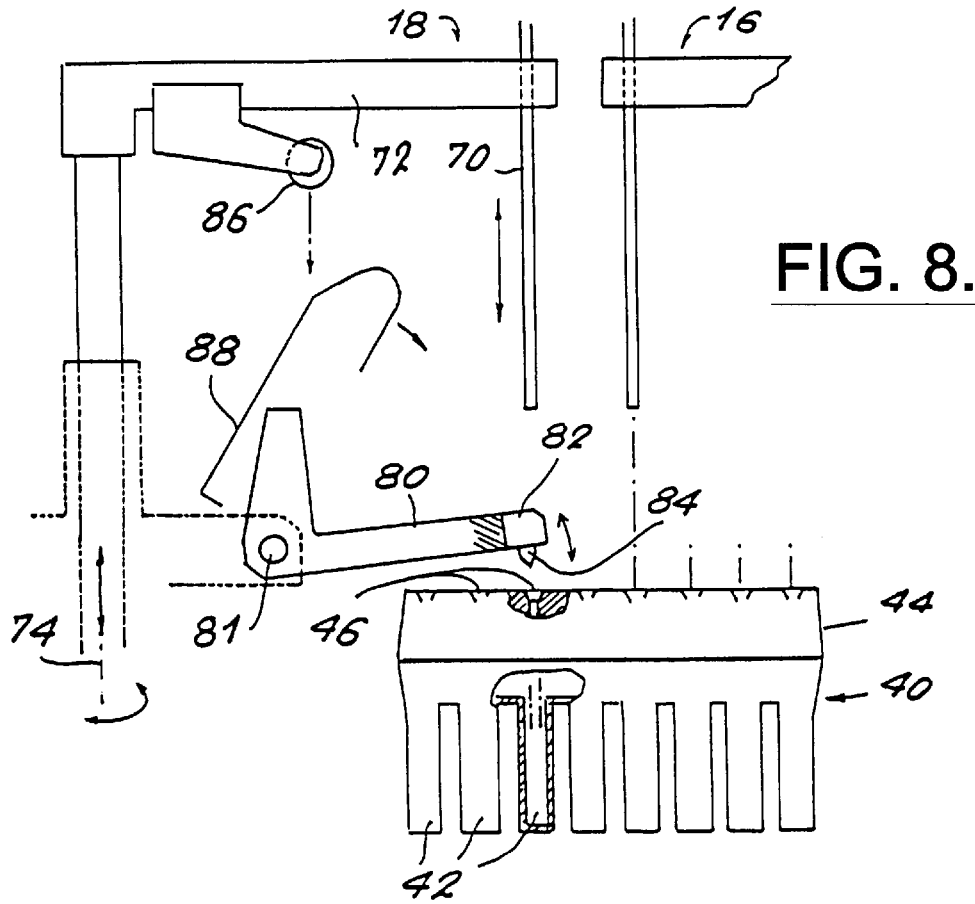
FIGS. 8 and 9 are diagrammatic elevation and plan views respectively of the means used for taking a quantity of sample or of reagent and for depositing it in a reaction well.
Figure 9:
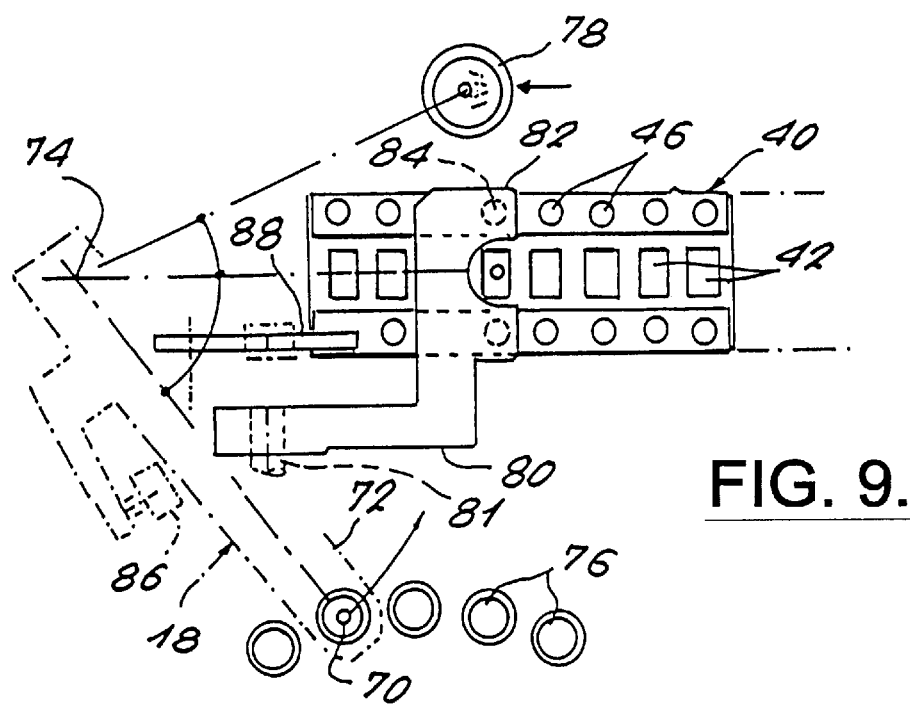

Naturally, the means 16 for taking a determined quantity of sample from tubes carried by the turntable 10, and the means 20 for taking a predetermined quantity of reagent from flasks carried by the turntable 14 are fitted with means for accurately positioning the reaction wells 42 identical to those of the means 18 for taking reagent and shown diagrammatically in FIGS. 8 and 9.

Figure 10:
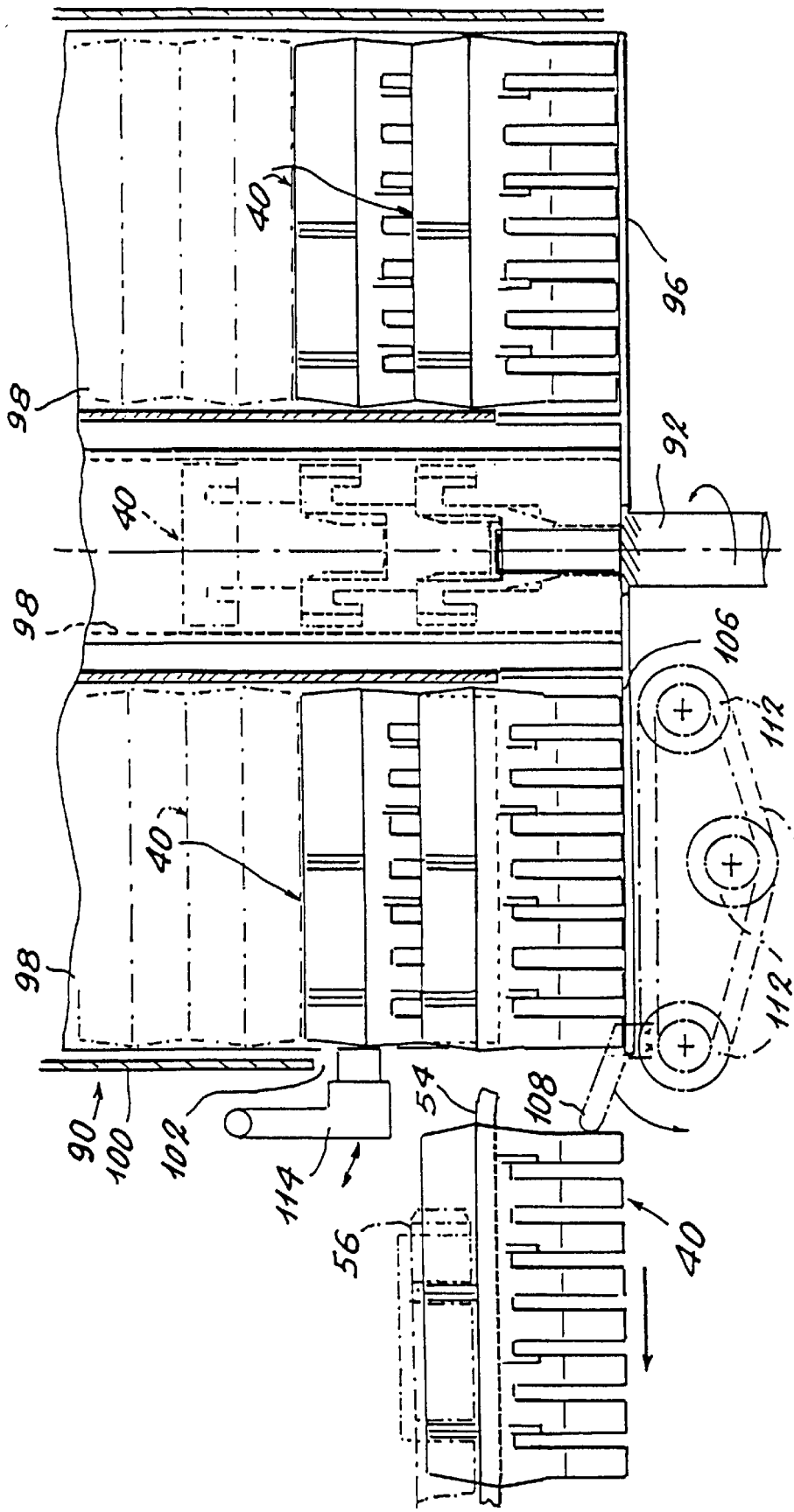
FIG. 10 is a fragmentary diagrammatic view in elevation of means for feeding the apparatus with reaction modules.

The means 26 for feeding the apparatus with reaction modules are shown diagrammatically in FIGS. 1 and 2, and in greater detail in FIG. 10. Essentially they comprise a magazine 90 mounted to rotate about a vertical axis 92 and displaceable in stepwise rotation about said axis by drive means (not shown).

The magazine 90 has vertical compartments 94, e.g. 12 compartments, each compartment being capable of containing a certain number of reaction modules 40 stacked vertically on one another, the number of modules per compartment being, for example, six and being capable of lying in the range five to ten, depending on the height of the feed magazine 90. The magazine 90 is essentially constituted by a circular bottom turntable 96 mounted to rotate about the axis 92 and carrying radial vertical partitions 98 defining between them the compartments 94 and receiving the stacks of reaction modules 40, the turntable 96 and its radial partitions 98 being located inside a stationary cylindrical case 100 having two vertically-extending openings through which the reaction modules 40 pass, one of the openings 102 being in line with the upstream end A of the track on which the reaction modules move through the apparatus, and the other opening 104 being at 90°, for example, relative to the first and facing towards the front face of the apparatus so as to enable an operator to load stacks of reaction modules 40 into the magazine.

In each compartment 94, the turntable 96 forming the bottom of the magazine includes a radial slot 106 that is relatively narrow and that allows a finger 108 to pass therethrough. The finger 108 is carried by a chain 110 passing over toothed wheels 112 disposed beneath the magazine 90, the chain 110 being in alignment with the upstream end A of the track on which the reaction modules move through the apparatus. On being driven in rotation by one of the toothed wheels 112, the chain drives the finger which serves to push out the reaction module 40 that is situated at the bottom of a stack contained in the compartment 94 which is radially in alignment with the upstream end A of the track 24. The bottom module 40 moves in a radially outwards direction so as to come to the upstream or inlet end A of the track 24, engage between the rails 54, and mesh with the cog belt 56.

When the bottom reaction module in a stack is thus ejected from the stack, the remainder of the stack moves down under gravity inside the compartment 94 until the reaction module which was immediately above the module that has just been ejected comes to rest on the turntable 96.

A tilting element 114 is mounted near the top end of the slot 102 through the cylindrical case 100 of the magazine and serves, in particular, to hold the reaction module situated immediately above the next module to be inserted into the apparatus and to detect when the last reaction module of a stack has dropped onto the bottom turntable 96, so as to cause the turntable subsequently to be rotated through one angular step, thereby bringing the following compartment 94 containing a stack of reaction modules into alignment with the end A of the track on which the modules move through the apparatus.

These successive rotations of the bottom turntable 96 about the axis 92 bring the empty compartments 94 successively into register with the opening 104 through the case 100, thereby enabling an operator to refill them with reagent modules.

In general, the apparatus operates as follows:

It is assumed that the tubes containing samples to be analyzed have been placed on the turntable 10, that flasks of appropriate reagents have been placed on the turntables 12 and 14, that stacks of reaction modules 40 have been loaded into the compartments 94 of the feed magazine 90, and that reaction modules 40 are engaged on the track 24 and are being moved stepwise along the track by the cog belt 56.

Firstly, immediately upstream from the means 16 for taking samples, a small quantity of a liquid for treating the surface of the reaction well is injected into each well, with this treatment serving to limit any risk of non-specific response associated with proteins of the sample being absorbed onto the material from which the reaction well is made. This may be done using an injection needle as shown diagrammatically at a in FIG. 2, which needle is connected by an electrically controlled valve and a pump to a tank of suitable liquid, which liquid may be a buffered solution of pH 6 and containing a wetting agent (optionally the washing solution used in the washing means 32).

When the reaction modules reach the means 16 for taking samples, a determined quantity of a sample to be analyzed is taken from a tube carried by the turntable 10 and is deposited in a reaction well of a module 40, then the modules are advanced by one step, a determined quantity of sample to be analyzed is again taken from a tube on the turntable 10 and deposited in the following reaction well, and so on. When the reaction wells reach the means 18, these means take a determined quantity of an appropriate reagent from a flask 76 on the turntable 12 and deposit it in a reaction well containing a sample to be analyzed, all the reaction modules advance through one step, and so on.

The assays are the same as those described in detail in the above-specified international application and, for single-reagent type assays, they essentially comprise depositing a quantity of sample and then a quantity of reagent in a reaction well, incubation until the reaction well reaches the first washing means 32, successive washes of the magnetic beads of the reagent, with the beads being held in the wells by magnetic attraction, then depositing a substrate that is specific to an enzyme in the reaction well, with the substrate being deposited by the last needle of the first washing means 32 (as described in the above-specified international application), enzyme incubation that takes place while the reaction well is travelling to the first means 30 for reading the results, where the magnetic beads are caused to settle by magnetic attraction and a light beam is passed through the reaction well towards an appropriate detector for determining the result of the assay on the basis of the light intensity received by the detector.

Dual-reagent type assays essentially comprise depositing a sample in a reaction well by the means 16, depositing a reagent in the well by the means 18, first incubation until the well reaches the first washing means 32, washing the magnetic particles constituting the first reagent, depositing a second reagent in the well as taken by the means 20 from a flask on the turntable 14, second incubation until the reaction well reaches the second washing means 32, washing the magnetic beads constituting the reagents and depositing a substrate specific to an enzyme, then enzyme incubation until the reaction well reaches the second means 30 for reading the result, where the magnetic beads are caused to settle by magnetic attraction and the result of the assay is detected from the light intensity received by a detector after the light has passed through the reaction well.

At the outlet from the second read means 30, the reaction wells are emptied of their contents by suction through a vertically movable needle 116 of the same type as that fitted to the washing means 32, and then the reaction modules 40 reach ejection means 28 which are constituted merely by a downwardly sloping chute leading to a bin 118.

As described in the above-specified international application, the needles of the means for taking samples and reagents are decontaminated by taking in and ejecting a decontamination liquid (e.g. "Tween"). To do this, the needle is lowered into a decontamination pot, it sucks up a certain quantity of decontamination liquid, and it ejects a portion thereof while keeping the remainder which is used to provide additional volume to the next quantity taken, e.g. of sample to be analyzed.

The decontamination and sample-taking functions can thus be combined to perform a function of automatically diluting the samples to be analyzed, which makes it possible to take account of variations in concentration that can be large (for example with tumor markers, concentration scales may vary over the range one to several hundred thousand).

This automatic dilution function consists in:

taking a quantity of sample from a tube on the turntable 10;

depositing the taken quantity of sample in a first reaction well together with a determined quantity of decontamination liquid;

then taking from said well a quantity of the mixture of sample and decontamination liquid;

depositing this taken quantity in the following well together with a new determined quantity of decontamination liquid once the wells have been advanced one step; and decontaminating the needle as mentioned above, with the assay subsequently being performed not on the sample contained in the first well which has served solely for the purpose of intermediate dilution, but on the diluted sample in the following well.

To simplify the structure of the apparatus of the invention and to reduce its cost, the two means 30 for reading the result are advantageously connected to a common light source.

For the same reasons, the two washing means 32 may be in transverse alignment relative to the track 24 along which the reaction modules move, and may comprise a common vertically displaceable support 120 on which both washing heads are mounted, which heads carry groups of needles for sucking up and injecting liquid in the reaction wells.

The washing heads are fed with washing liquid from a common can 122 housed in the bottom of the apparatus. The means for decontaminating the sample-taking and reagent-taking needles are fed with decontamination liquid from a common can 124 likewise housed in the bottom portion of the apparatus, next to the first-mentioned can 122.

Figure 11:
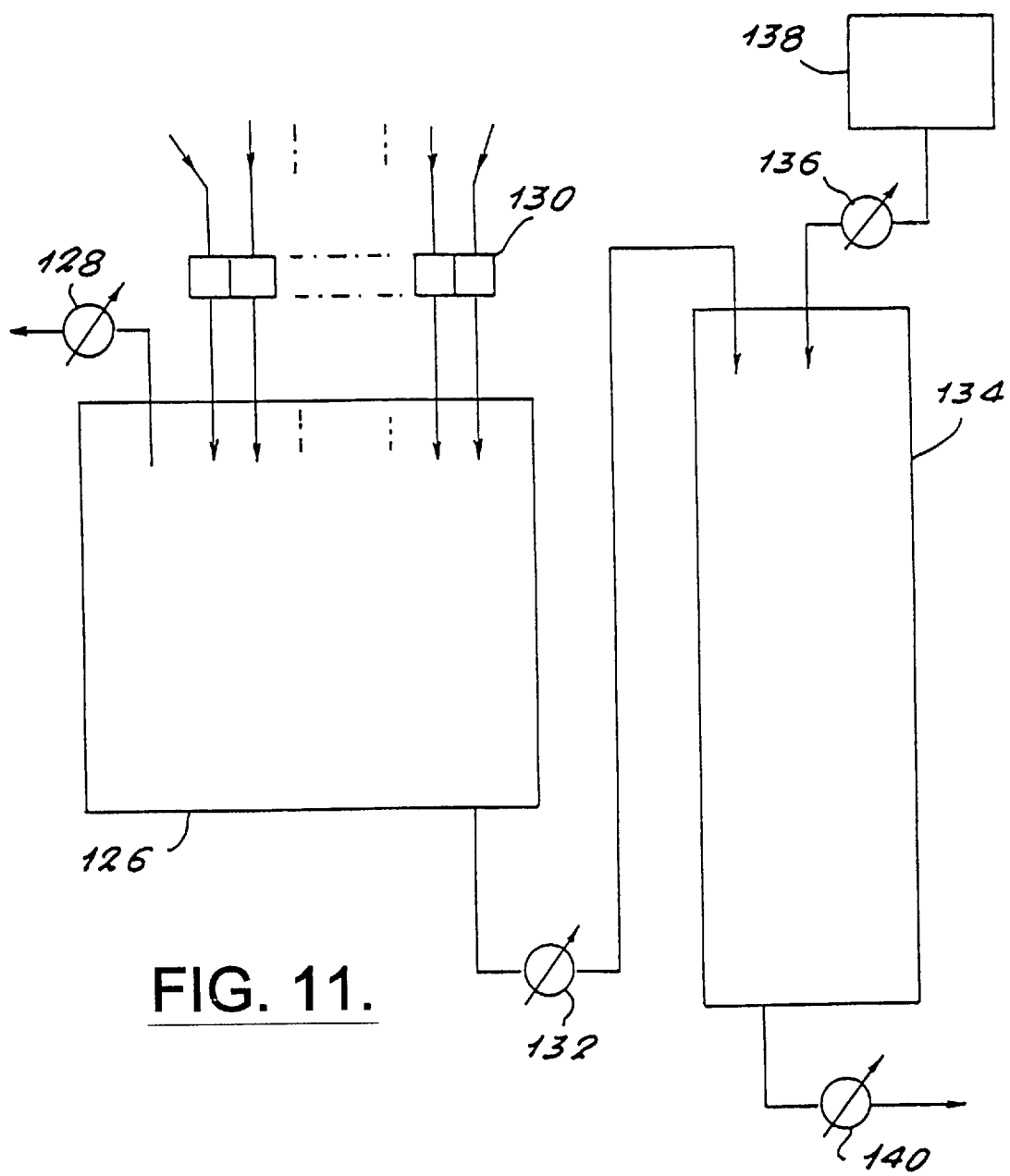
FIG. 11 is a fragmentary diagrammatic view of means for recovering the liquids used in the apparatus of the invention.

The washing and decontamination liquids and the contents of the reaction wells at the downstream end B of the track are recovered by suction and they are made safe by the system shown in FIG. 11.

This system comprises a closed tank 126 which can be maintained at reduced pressure by means of a vacuum pump 128. The suction needles of the washing means 32, the decontamination pots 78 of the sample- or reagent-taking means 16, 18, and 20, and the needle 116 for removing the contents from the reagent wells are all connected to the tank 126 via electrically controlled valves 130. Sequential commands applied to these valves make it possible merely by connecting a suction needle or a pot 78 to the tank 126 to suck up the washing liquid or the decontamination liquid used or the contents of a reaction well, and to transfer it into the tank 126.

The tank is connected by a pump 132 to a buffer tank 134 itself filled with liquid for making safe (e.g. bleach) via a pump 136 and a tank 138.

The bottom portion of the tank 134 is connected by a pump 140 to discharge means of the sink or drain type.

The tanks 126 and 134 are also fitted with detectors to detect when they are full and prevent overflow.

The operation of this system follows clearly from the above description:

As soon as the liquid in the tank 126 reaches a determined level, it is transferred into the tank 134 and made safe by a determined quantity of the liquid supplied by the pump 136 from the tank 138.

When the buffer tank 134 contains a determined quantity of liquid that has been made safe, the pump 140 is put into operation and the liquid is discharged to a sink or drain.

Finally, the operation of the apparatus of the invention is also improved by the tubes of samples to be analyzed on the turntable 10 being identified by means of bar codes. A bar code reader disposed in the immediate vicinity of the periphery of the turntable 10 makes it possible to identify without risk of error the samples which are taken from the tubes and deposited in the reaction wells. Identical means can be used for identifying the flasks of reagents carried by the turntables 12 and 14.

We claim:

1. Automatic immunological assay apparatus, comprising:
   (a) at least one module comprising a plurality of longitudinally juxtaposed reaction wells;
   (b) means for providing at least one sample to be analyzed;
   (c) means for providing at least one magnetic bead reagent;
   (d) means for introducing determined quantities of sample and reagent into a reaction well;
   (e) means for reading assay results;
   (f) an open loop track comprising fixed elements, which track supports and guides the modules;
   (g) a chain or belt that extends along the track and engages the modules to move the modules from an upstream end of the track to a downstream end of the track;
   (h) automatic module feed means and module ejection means being provided respectively at the upstream end and at the downstream end of said track;
   (i) means for moving the reaction wells stepwise in a downstream direction past the means for introducing sample and reagent and the means for reading the results; and
   (j) two magnetic bead washing heads respectively disposed at separate positions on opposite branches of the track for washing magnetic beads contained in reaction wells of a module positioned under the respective washing head, with both washing heads being movable between a first, rest position, and a second, working position, and being carried by a common support for vertical displacement between the two positions,
   wherein the means for reading assay results comprises two systems for optically reading assay results, said systems being spaced apart from each other on the track with a first of the two systems being adapted for reading the results of single-reagent type assays and a second of the two systems being adapted for reading the results of dual-reagent type assays.

2. Apparatus according to claim 1, wherein the modules are driven in translation and move by sliding on the above-mentioned fixed elements.

3. Apparatus according to claim 1, wherein the fixed elements for supporting and guiding modules are rails between which the wells of the modules extend vertically.

4. Apparatus according to claim 1, wherein the track on which the modules move is U-shaped.

5. Apparatus according to claim 4, wherein the chain or belt is guided on the inside rail of an track.

6. Apparatus according to claim 1, including means for accurately positioning wells, said positioning means comprising moving abutments co-operating with top sides of the modules.

7. Apparatus according to claim 4, wherein the two washing heads are disposed on each of the two branches of the U-shaped track.

8. Apparatus according to claim 1, including means provided upstream from the sample-taking means to inject a liquid into the reaction wells for pretreating the surface of the reaction wells.

9. Apparatus according to claim 1, wherein the two systems for optically reading assay results, are connected to a common light source.

10. Apparatus according to claim 1, including means for sucking out the contents from the reaction wells at the downstream end of the well displacement track.

11. Apparatus according to claim 10, wherein the means for sucking up substances contained in the reaction wells are connected via electrically controlled valves to a suction tank.

12. Apparatus according to claim 1, wherein the means for taking samples co-operate with decontamination means to constitute means for automatically diluting the samples taken.

13. Apparatus according to claim 3, wherein the reaction modules include top longitudinal rims which can rest on the rail.

14. Apparatus according to claim 13, wherein said top longitudinal rims include orifices on either side of each well, and positioning fingers that can engage with the orifices are mounted on moving elements organized in association with the means for introducing samples or reagents.

15. Apparatus according to claim 13 wherein the top longitudinal rims of the reaction modules include vertical ribs.

16. Apparatus according to claim 1, wherein the reaction modules are vertically stackable and are stored in vertical stacks in compartments in a feed magazine.

* * * * *